United States Patent
Jenkins et al.

(10) Patent No.: US 9,625,356 B2
(45) Date of Patent: Apr. 18, 2017

(54) FLUID FLOW SAMPLING DEVICE

(71) Applicant: Universal Analyzers Inc., Carson City, NV (US)

(72) Inventors: Michael Jenkins, Carson City, NV (US); Phil Harris, Calgary (CA); Ted Barben, Carson City, NV (US)

(73) Assignee: UNIVERSAL ANALYZERS INC., Carson City, NV (US)

( * ) Notice: Subject to any disclaimer, the term of this patent is extended or adjusted under 35 U.S.C. 154(b) by 205 days.

(21) Appl. No.: 14/326,946

(22) Filed: Jul. 9, 2014

(65) Prior Publication Data

US 2015/0075302 A1  Mar. 19, 2015

Related U.S. Application Data

(63) Continuation-in-part of application No. 13/646,197, filed on Oct. 5, 2012.

(60) Provisional application No. 61/558,181, filed on Nov. 10, 2011.

(51) Int. Cl.
  *G01N 1/02* (2006.01)
  *G01N 1/20* (2006.01)
  *G01N 1/16* (2006.01)
  *G01N 1/22* (2006.01)

(52) U.S. Cl.
  CPC .............. *G01N 1/20* (2013.01); *G01N 1/16* (2013.01); *G01N 1/2035* (2013.01); *G01N 1/2205* (2013.01)

(58) Field of Classification Search
  CPC ...... G01N 1/02; G01N 1/2035; G01N 1/2205; G01N 2001/2285; G01N 1/16; G01N 1/20
  See application file for complete search history.

(56) References Cited

U.S. PATENT DOCUMENTS

| | | | |
|---|---|---|---|
| 3,561,487 A | 2/1971 | Reed, Jr. | |
| 3,850,449 A | 11/1974 | Link et al. | |
| 4,018,089 A * | 4/1977 | Dzula | G01N 1/2035 73/863.58 |

(Continued)

FOREIGN PATENT DOCUMENTS

| | | |
|---|---|---|
| JP | 2010/133918 | 6/2010 |
| KR | 10/2011/0120723 | 11/2011 |
| WO | WO 97-38776 | 10/1997 |

*Primary Examiner* — Daniel S Larkin
(74) *Attorney, Agent, or Firm* — Thorpe North & Western LLP

(57) ABSTRACT

A fluid flow sampling device comprises a housing and a sleeve disposed in the housing having openings corresponding to an inlet and an outlet of the housing. The sleeve is movable relative to the housing to an open position and a closed position. The open position aligns the openings of the sleeve with the inlet and the outlet to allow fluid to flow into the inlet, through the sleeve, and out of the outlet. The closed position blocks the inlet and/or the outlet with a portion of the sleeve such that fluid is prevented from flowing through the sleeve. A coalescent filter is disposed in the sleeve between the inlet and the outlet to allow some fluid to pass through the filter for sampling and to allow another portion of fluid to flow past the filter and out of the outlet to carry away coalescent material on the filter. Additionally, a sample outlet port facilitates removal of fluid from the sampling device for sampling.

10 Claims, 13 Drawing Sheets

(56) References Cited

U.S. PATENT DOCUMENTS

| | | | | |
|---|---|---|---|---|
| 4,391,152 A | * | 7/1983 | Ellett | G01N 1/2035 |
| | | | | 73/863.84 |
| 4,404,284 A | * | 9/1983 | Heider | C12M 41/34 |
| | | | | 435/287.1 |
| 5,601,713 A | * | 2/1997 | Mayeaux | B01D 17/045 |
| | | | | 210/426 |
| 5,777,241 A | * | 7/1998 | Evenson | G01N 1/2258 |
| | | | | 73/863.11 |
| 5,800,597 A | * | 9/1998 | Perrotta | B01D 46/24 |
| | | | | 55/318 |
| 6,357,304 B1 | * | 3/2002 | Mayeaux | G01N 1/2035 |
| | | | | 73/863.12 |
| 6,701,794 B2 | | 3/2004 | Mayeaux | |
| 6,904,816 B2 | | 6/2005 | Mayeaux | |
| 7,004,041 B2 | | 2/2006 | Mayeaux | |
| 7,267,322 B1 | * | 9/2007 | Luby | G01D 11/245 |
| | | | | 251/149 |
| 2003/0178350 A1 | | 9/2003 | Harris et al. | |
| 2005/0121401 A1 | | 6/2005 | Walton et al. | |

* cited by examiner

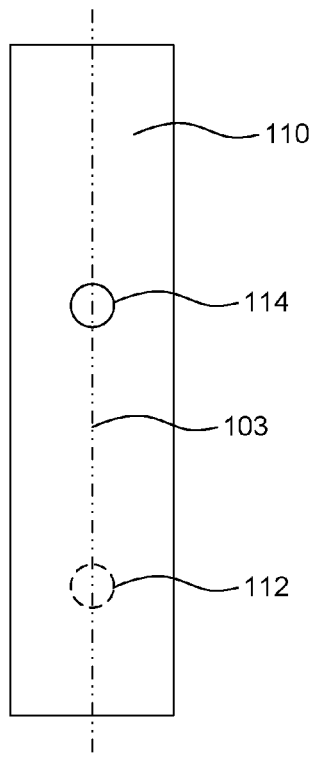 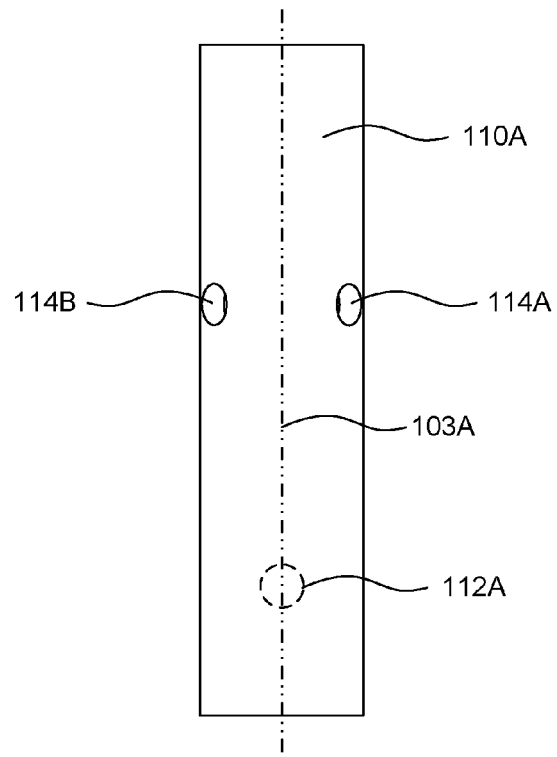
FIG. 3A  FIG. 4A
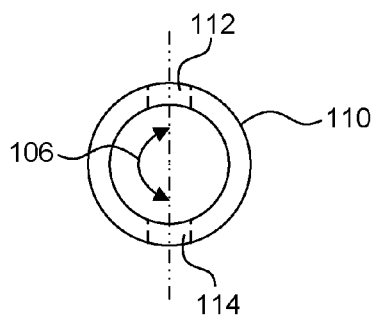 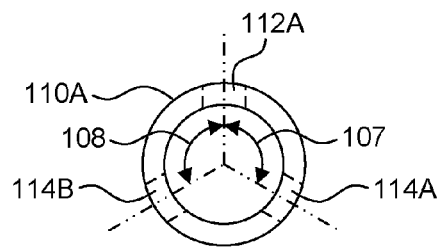
FIG. 3B  FIG. 4B

FLUID FLOW SAMPLING DEVICE

RELATED APPLICATIONS

This application is a Continuation-In-Part of U.S. patent application Ser. No. 13/646,197, filed Oct. 5, 2012, which claims the benefit of U.S. Provisional Patent Application No. 61/558,181, filed Nov. 10, 2011, each of which is incorporated herein by reference.

BACKGROUND

A variety of gases and liquids carried by pipes or conduits often require sampling and analysis. For example, fluids found in refineries, petrochemical pipelines, natural gas pipelines, etc. are commonly sampled and analyzed for various purposes. Some sampling devices extend into a fluid conduit to enable extraction of fluid from the conduit as the fluid flows past the sampling device. Often, impurities can be present in the fluid and it may be desirable to isolate fluid material to be sampled and analyzed from impurities entrained in the fluid. Sampling devices therefore can include coalescent elements to remove entrained liquids from a gas. In some sampling devices, the coalescent element can become clogged with coalescent material, which reduces the effectiveness of the sampling device and can require removal and replacement of the coalescent element. It is therefore desirable to maintain the coalescent element free of coalescent material to the extent possible. For example, some sampling devices are configured to allow the coalescent material to "drip" or "run off" the coalescent element under the effect of gravity. This is a passive approach to removal of the coalescent material from the coalescent element and may not always be effective.

BRIEF DESCRIPTION OF THE DRAWINGS

FIG. 3A is a side view of a housing illustrating an inlet and outlet configuration in accordance with an example of the present disclosure.

FIG. 3B is a top view of the inlet and outlet configuration of FIG. 3A.

FIG. 4A is a side view of a housing illustrating an inlet and outlet configuration in accordance with another example of the present disclosure.

FIG. 4B is a top view of the inlet and outlet configuration of FIG. 4A.

DETAILED DESCRIPTION

Figure 1A:
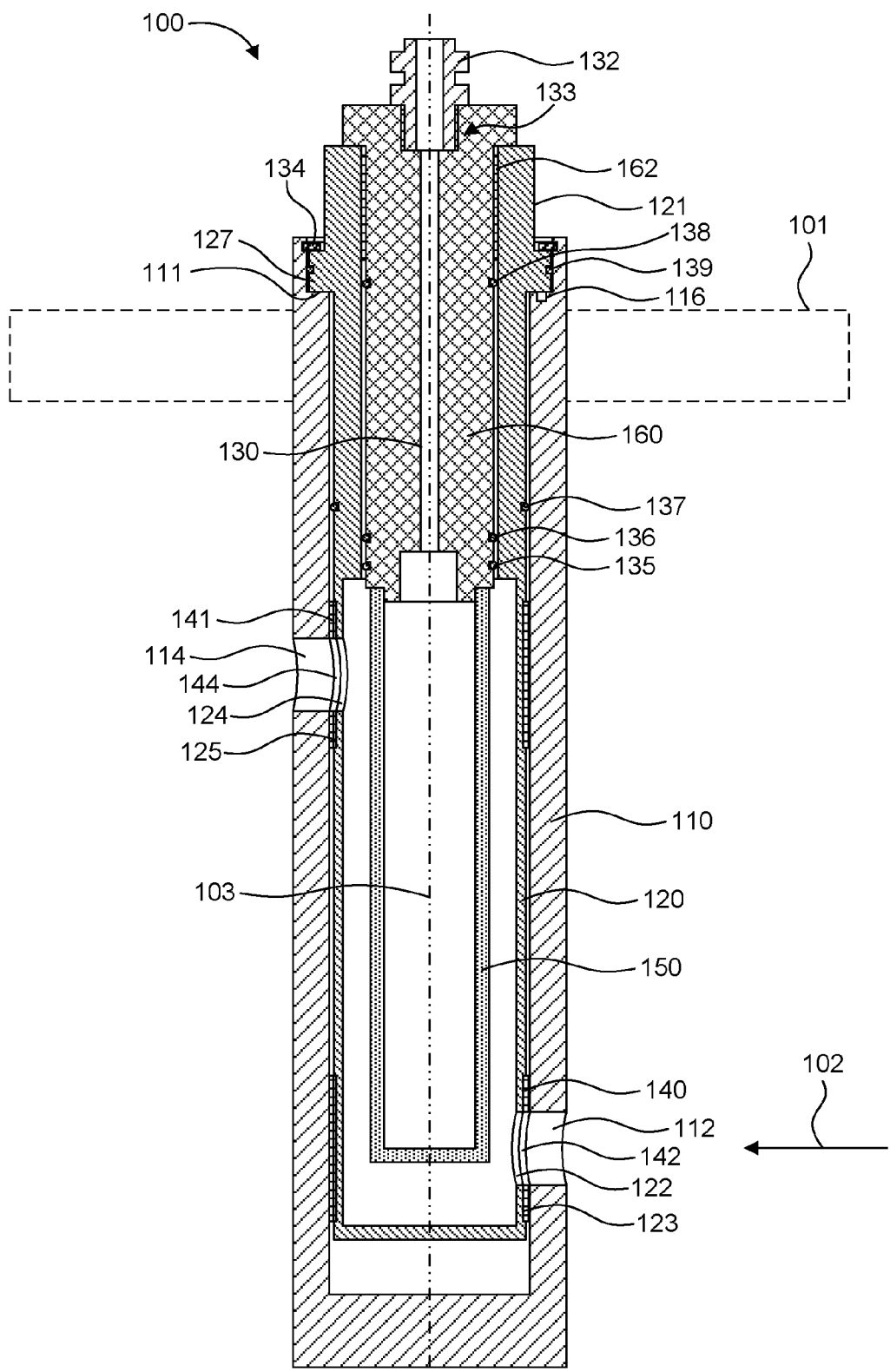
FIG. 1A is a side cross-sectional view of a fluid flow sampling device in an open position in accordance with an example of the present disclosure.

Reference will now be made to certain examples, and specific language will be used herein to describe the same. Examples discussed herein set forth a fluid flow sampling device that can enable sampling of fluid from a fluid conduit. In particular examples, the fluid flow sampling device can provide active removal of coalescent material from a coalescent element. Additionally, in some examples the fluid flow sampling device can enable removal of the coalescent element from the device for inspection or replacement.

Specifically, a fluid flow sampling device can comprise a housing having a fluid inlet and a fluid outlet longitudinally separated from one another along an axis of the housing. The fluid flow sampling device can also comprise a sleeve disposed in the housing having openings corresponding to the inlet and the outlet of the housing, the sleeve being movable relative to the housing to an open position and a closed position. The open position aligns the openings of the sleeve with the inlet and the outlet of the housing to allow fluid to flow into the inlet, through the sleeve, and out of the outlet. The closed position blocks the inlet and/or the outlet with a portion of the sleeve such that fluid is prevented from flowing through the sleeve. It is noted that the presence of small leaks or incomplete sealing when in the closed position would still be considered as preventing fluid flow through the sleeve. The fluid flow sampling device can further comprise a coalescent filter disposed in the sleeve between the inlet and the outlet to allow a sampling portion of the fluid to pass through the filter and to allow a bypass portion of the fluid to flow past the filter and out of the outlet to carry away coalescent material on the filter. Additionally, the fluid flow sampling device can comprise a sample outlet port on a side of the housing to facilitate removal of the sampling portion of the fluid from the sampling device for sampling.

In another example, a fluid flow sampling device can comprise a fluid inlet positionable in a middle third of a fluid conduit. The fluid flow sampling device can also comprise a fluid outlet longitudinally separated from the fluid inlet, and in one embodiment, it can be positionable in an outer third of the fluid conduit. The fluid flow sampling device can also comprise a coalescent filter disposed between the inlet and the outlet to allow a sampling portion of fluid to pass through the filter and to allow a bypass portion of the fluid to flow past the filter and out of the outlet to carry away coalescent material from the filter. Additionally, the fluid flow sampling device can comprise a sample outlet port to facilitate removal of the sampling portion of the fluid from the sampling device for sampling.

In yet another example, a fluid flow sampling device can comprise a housing having a fluid inlet and a fluid outlet longitudinally separated from one another along an axis of the housing. The fluid flow sampling device can also comprise a coupling portion on the housing to couple the fluid flow sampling device to a fluid conduit, and optionally, the fluid inlet can be positioned in a middle third of the fluid conduit. The fluid inlet and the fluid outlet are fluidly coupled to one another such that a bypass portion of fluid flow in the fluid conduit enters the inlet, flows through the housing, and exits the outlet. A sampling portion of the fluid flow can be extractable from within the housing to a location outside of the fluid conduit. In addition, the fluid flow sampling device can comprise a sample outlet port to facilitate extraction of the sampling portion of the fluid from within the housing for sampling.

Furthermore, a method for configuring a fluid flow sampling device in accordance with the principles herein can comprise obtaining a housing having a fluid inlet and a fluid outlet longitudinally separated from one another along an axis of the housing, and a sample outlet port to facilitate extraction of fluid from within the housing. The method can also comprise obtaining a coalescent filter. Additionally, the method can comprise disposing the coalescent filter in the housing between the inlet and the outlet to allow a sampling portion of fluid to pass through the filter extraction via the sample outlet port for sampling and to allow a bypass portion of the fluid to flow past the filter and out of the outlet to carry away coalescent material on the filter. Optionally, the method can further comprise obtaining a sleeve having openings corresponding to the fluid inlet and the fluid outlet of the housing, the sleeve being movable relative to the housing to an open position and a closed position. The open position aligns the openings of the sleeve with the fluid inlet and the fluid outlet of the housing to allow fluid to flow into the fluid inlet, through the sleeve, and out of the fluid outlet. The closed position blocks the fluid inlet and/or the fluid outlet with a portion of the sleeve such that fluid is prevented from flowing through the sleeve. This sleeve can then be disposed in the housing at least substantially around the coalescent filter. Again, it is noted that the presence of small leaks or incomplete sealing when in the closed position would still be considered as preventing fluid flow through the sleeve.

With these general examples set forth above, it is noted in the present disclosure that when describing the fluid flow sampling devices described herein, or their related methods, each of these descriptions are considered applicable to the other, whether or not they are explicitly discussed in the context of that embodiment. For example, in discussing the fluid flow sampling device per se, the method embodiments are also included in such discussions, and vice versa.

Furthermore, various modifications and combinations can be derived from the present disclosure and illustrations, and as such, the following figures should not be considered limiting. It is noted that reference numerals in various FIGS. will be shown in some cases that are not specifically discussed in that particular figure. Thus, discussion of any specific reference numeral in a given figure is applicable to the same reference numeral of related figures shown herein.

Figure 1B:
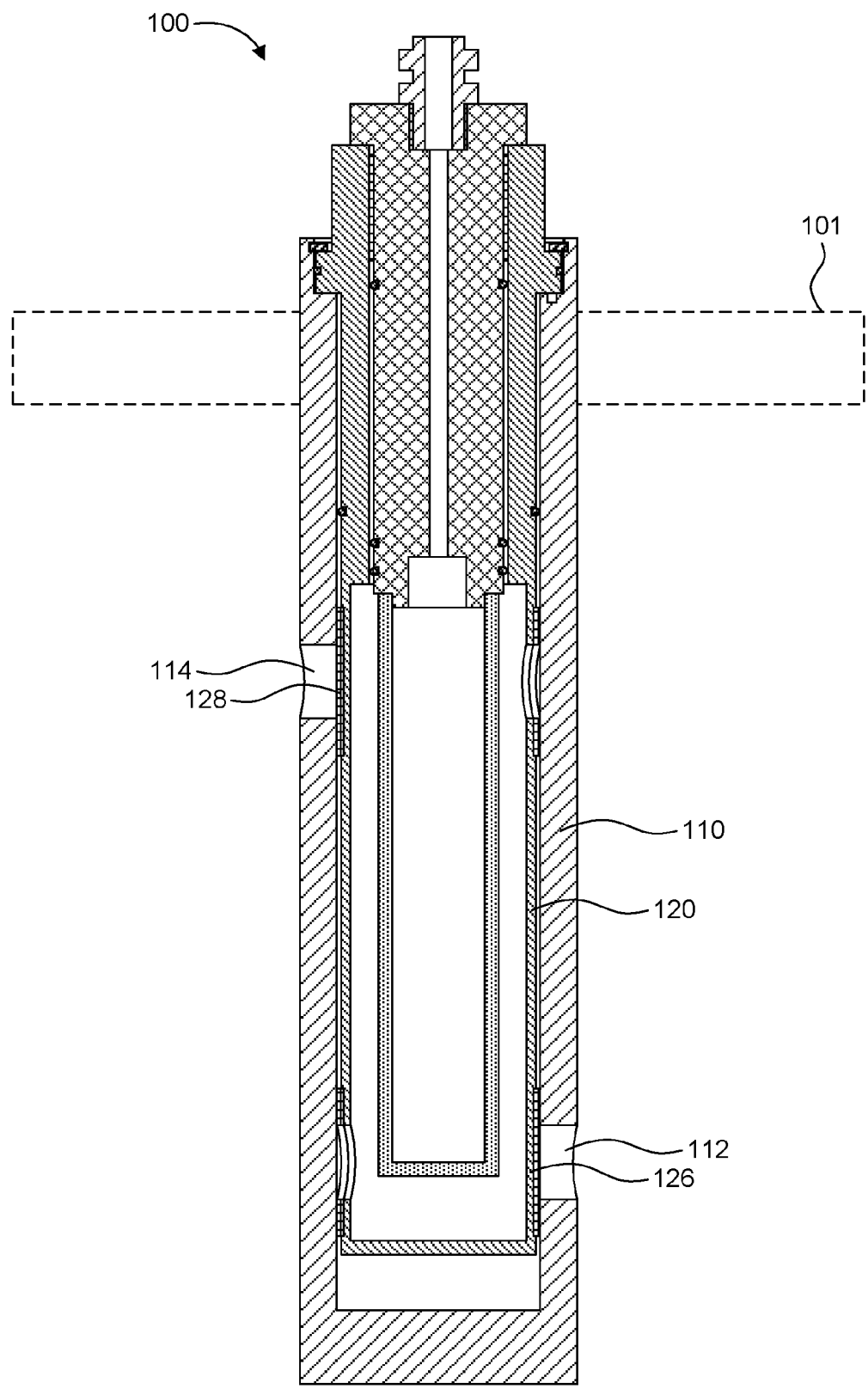
FIG. 1B is the fluid flow sampling device of FIG. 1A in a closed position.

Illustrated in FIGS. 1A and 1B is fluid flow sampling device 100. The fluid flow sampling device 100 can be mounted, installed, or otherwise associated with a fluid conduit 101, such as a pipe. For simplicity, only a portion of a wall of the fluid conduit 101 is shown in FIGS. 1A and 1B. Typically, the fluid flow sampling device 100 is supported by the fluid conduit 101 in a manner that allows the fluid flow sampling device to extend into an interior of the fluid conduit, though other arrangements are also included within the scope of the present disclosure.

The fluid flow sampling device 100 can include housing 110. The housing 110 can be coupled to the fluid conduit 101 by any suitable means, such as by a threaded interface, a weld, or an adhesive, individually or in any combination. In use, the conduit 101 may be pressurized by a fluid contained therein. For example, the fluid can be pressurized from about 500 psi to about 1500 psi and, more particularly, from about 800 psi to about 1000 psi, though these ranges are provided for exemplary purposes only. In one aspect, the sampling device 100 helps to form a pressure barrier for the pressurized fluid within the conduit. Thus, suitable couplings of the conduit 101 and the housing 110 and between various components of the sampling device 100 discussed herein can be configured to withstand the fluid pressure within the conduit 101.

Figure 2:
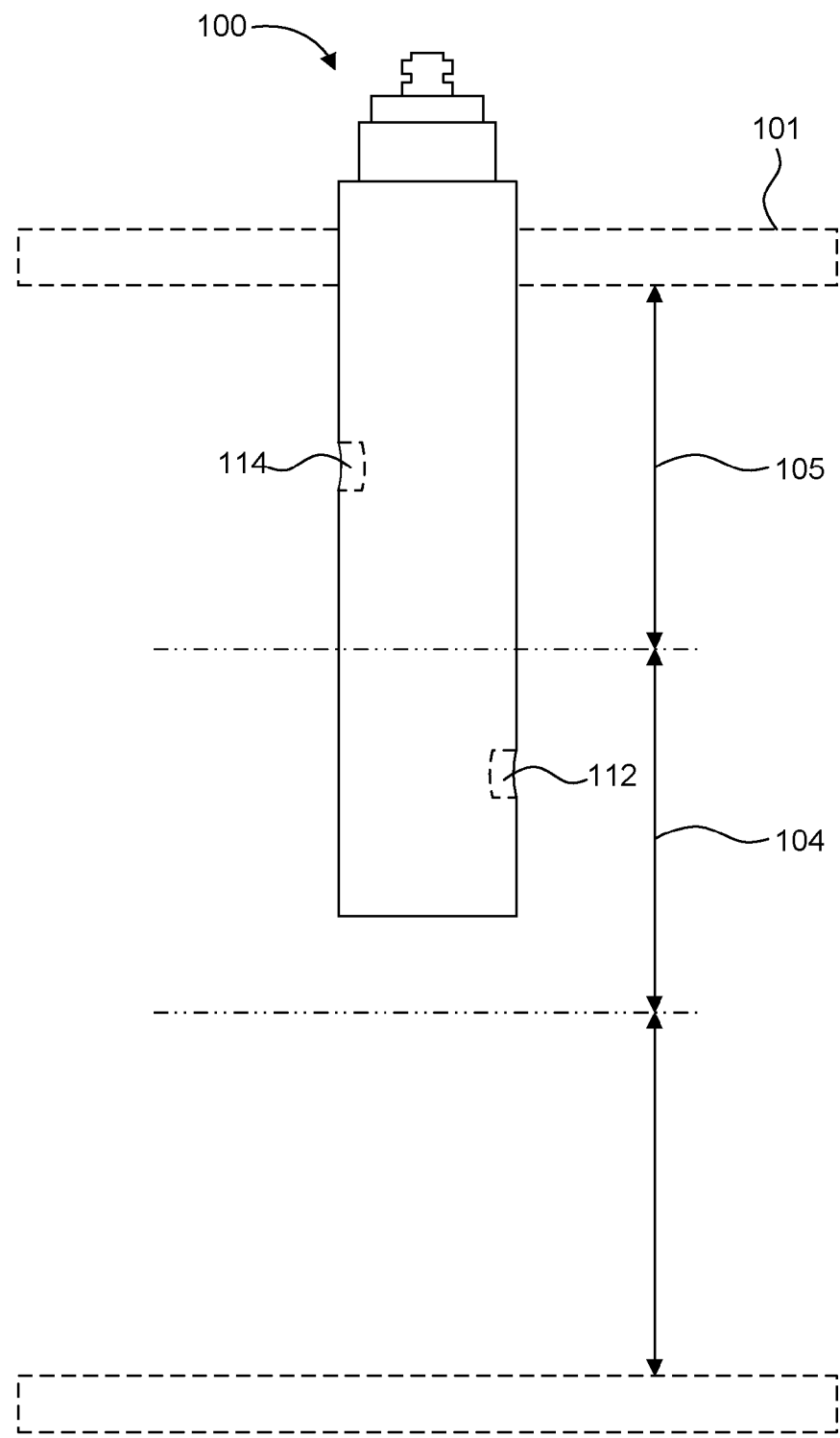
FIG. 2 is the fluid flow sampling device of FIG. 1A illustrating locations of a fluid inlet and outlet within a fluid conduit.

The housing 110 can have a fluid inlet 112 and a fluid outlet 114. The fluid inlet will sometimes be referred to simply as "inlet" and the fluid outlet will sometimes be referred to simply as "outlet." Some fluid flowing in the conduit 101 can enter the sampling device 100 via the fluid inlet 112 and can exit the sampling device via the fluid outlet 114. The fluid inlet 112 can be oriented in the fluid conduit 101 facing generally "upstream," such that fluid flowing in direction 102 can enter the fluid inlet 112. The fluid outlet 114 can be oriented in the fluid conduit 101 facing generally "downstream," such that fluid flowing out of the fluid outlet 114 can readily rejoin fluid flowing in the fluid conduit 101. This positioning of the inlet 112 and the outlet 114 relative to one another can induce fluid flow through the housing 110 from the inlet 112 to the outlet 114 resulting from a pressure difference between the inlet 112 and the outlet 114. In one aspect, the fluid inlet 112 and the fluid outlet 114 can be longitudinally separated from one another along an axis 103 of the housing 110. This longitudinal separation can allow the fluid to flow through the housing in a direction generally parallel to the axis 103. In a particular aspect, the housing 110 can be of an elongate configuration to accommodate or facilitate a suitable longitudinal separation of the fluid inlet 112 and the fluid outlet 114. As illustrated in FIG. 2, the fluid inlet 112 can be positionable in a middle third 104 of the fluid conduit 101. Additionally, the fluid outlet 114 can be positionable in an upper third 105 of the fluid conduit 101, though this is not required.

Referring to FIGS. 3A and 3B, side and top views of the housing 110 are illustrated. Specifically, the perspective of the FIG. 3A side view is directed "upstream," such that the outlet 114 is visible and the inlet 112 is hidden. The inlet 112 and the outlet 114 are each disposed on a side of the housing and are each oriented substantially perpendicular to the axis 103. In this case, the inlet and the outlet are disposed on opposite sides of the housing. As illustrated in FIG. 3B, the inlet and the outlet are disposed at an angle 106 of about 180 degrees from one another about the axis 103, though other angles may also be used, e.g., 90 degrees, 120 degrees, etc.

FIGS. 4A and 4B illustrate another embodiment of an outlet configuration for a fluid flow sampling device. Due to the fluid dynamics involved in fluid flow around an object, eddy currents can form on the downstream side of the object. Eddy currents can cause buffeting, which can inhibit fluid flow out of an outlet on a downstream side of a housing of the present disclosure. Thus, to improve fluid flow out an outlet, a housing 110A can include an outlet 114A positioned outside of an eddy current forming area on the downstream side of the housing 110A. The positioning of the outlet 114A can be defined by an angle 107 relative to an inlet 112A (oriented on an upstream side of the housing 110A). The angle 107 can be any angle that positions the outlet 114A outside of an eddy current area on the downstream side of the housing 110A. Additionally, a second fluid outlet 114B can be disposed at an angle 108 relative to the inlet 112A about the axis 103A. As with the outlet 114A, the outlet 114B can be any angle that positions the outlet 114B outside of an eddy current area on the downstream side of the housing 110A. In one aspect, the angle 107 and/or the angle 108 can be from about 90 degrees to about 175 degrees. In a particular aspect, the angle 107 and/or the angle 108 is about 120 degrees. In another particular aspect (an embodiment of which is illustrated in FIGS. 8A-8D), the angle 107 and/or the angle 108 is about 90 degrees. This can locate outlet 114A and/or 114B at a high velocity point in the fluid flowing around the sampling device, which can reduce or minimize buffeting effects from eddy currents. Although the outlet 114A and the outlet 114B are longitudinally separated from the inlet 112A along the axis 103A, the outlet 114A and the outlet 114B may or may not be at the same longitudinal distance from the inlet 112A.

In general, an inlet and an outlet can be of any suitable size or shape and may or may not be the same size or shape. In one aspect, an inlet and an outlet can have openings that are of substantially the same size area. In another aspect, an outlet can have an opening area size that is greater than an opening area size of an inlet. With continued reference to FIGS. 4A and 4B, the opening area sizes of outlets 114A and 114B may or may not be the same. Furthermore, the combined opening areas of outlets 114A and 114B may or may not be the same as an opening area of inlet 112A. In one aspect, the combined opening areas of outlets 114A and 114B can be greater than or equal to the opening area of inlet 112A.

With further reference to FIGS. 1A and 1B, fluid that enters the housing 110 can be withdrawn from the sampling device 100 by an internal conduit 130. In this case, the internal conduit 130 is substantially aligned with the longitudinal axis 103 and extends through an interior support member 160 disposed inside a sleeve 120, which can be disposed in the housing 110. The internal conduit 130 can be fluidly coupled to an interior of the housing 110 (or, more specifically in this case, to an interior of the sleeve 120) and to an exterior of the sampling device 100, for example, via a sample outlet port 133 that is substantially aligned with the internal conduit 130 and the longitudinal axis 103. The sampling device 100 can include a fitting 132 coupled to the sample outlet port 133 that can interface with a tube or pipe (not shown) for transporting a fluid sample from the device 100 to a reservoir or testing station for analysis.

The sleeve 120 can have openings 122, 124 corresponding to the inlet 112 and the outlet 114 of the housing 110. The sleeve 120 can be movable relative to the housing 110 to an open position (shown in FIG. 1A) and a closed position (shown in FIG. 1B). In one aspect, the sleeve 120 can be rotatably movable about the axis 103 to the open and closed positions. The open position aligns the openings 122, 124 of the sleeve 120 with the inlet 112 and the outlet 114 of the housing 110 to allow fluid to flow into the inlet 112, through the sleeve 120, and out of the outlet 114. The closed position blocks the inlet 112 and the outlet 114 with a portion 126, 128 of the sleeve 120 such that no fluid can flow through the sleeve 120. Thus, rotation of the sleeve 120 to the open position can allow sampling fluid to be withdrawn from the conduit 101 via the sampling device 100 and rotation of the sleeve 120 to the closed position can prevent fluid from being withdrawn from the conduit by isolating the interior of the sleeve from the fluid flow in the conduit. The sleeve 120 can be manipulated at a location 121 external to the fluid conduit 101 to rotate the sleeve 120 between the open and closed positions. For example, the sleeve 120 can be configured with a handle or a wrench interface to enable rotation of the sleeve 120.

The sleeve 120 and the housing 110 can include features that enable rotation of the sleeve relative to the housing. For example, the housing 110 can include a shelf 111 configured to interface with a bottom side of a tab 127 of the sleeve 120. The housing 110 can also be configured to extend beyond the tab 127 and to capture a C-clip 134 that interfaces with a top side of the tab 127. In this configuration, relative movement of the sleeve 120 and the housing 110 is constrained in all directions except for rotation about the axis 103.

Figure 5:
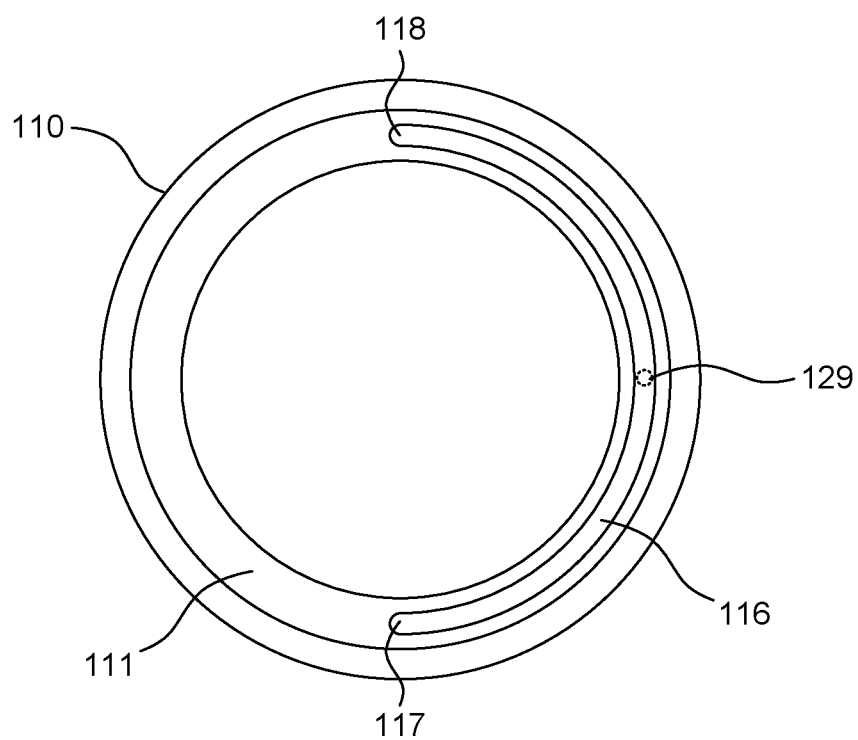
FIG. 5 is a top view of a housing illustrating features configured to limit relative rotational movement of the housing and a sleeve.

In one aspect, however, even the relative rotational movement of the sleeve 120 and the housing 110 can be limited. This is illustrated more particularly in FIG. 5, which shows a top view of the housing 110, and with additional reference to FIGS. 1A and 1B. The housing 110 can include an arcuate channel 116 in the shelf 111. The channel 116 can be configured to interface with an extension 129 from the tab 127. During relative rotation, the extension 129 can move within the channel 116 between ends 117, 118 of the channel 116, which limits the range of rotation of the sleeve 120 relative to the housing 110. The rotational limits can correspond to the open position at one end and the closed position at the opposite end. As shown, the channel 116 permits up to 180 degrees of rotation. Thus, the sleeve can rotate up to 180 degrees between a fully open position and a completely closed position. It should be recognized, however, that the range of motion limitation need not be 180 degrees. For example, a range of motion limitation of 90 degrees or less between the open and closed positions may be suitable for the sampling device 100 illustrated in FIGS. 1A and 1B, depending on the size of the inlet 112 and outlet 114. With rotational limits, a user can be informed of whether the sampling device 100 is in an open or a closed position.

With further reference to FIGS. 1A and 1B, when in the closed position, the portions 126, 128 of the sleeve 120 can be subjected to the fluid pressure within the conduit 101. Thus, the sleeve 120 can be configured to withstand the fluid pressure within the conduit 101 when in the closed position such that little or no fluid can penetrate the pressure boundary formed by the sleeve 120 and the housing 110. To improve the integrity of this pressure boundary or, in other words, to minimize leakage between the sleeve 120 and the housing 110, pressure seals 140, 141 can be disposed between the sleeve 120 and the housing 110. The pressure seals 140, 141 can include openings 142, 144 corresponding to the openings 122, 124 of the sleeve 120 and the inlet 112 and the outlet 114 of the housing 110. In one aspect, the pressure seals 140, 141 can be constrained to move with the sleeve 120, such that rotation of the sleeve causes rotation of the pressure seals. In a particular aspect, the pressure seals 140, 141 can be fitted into channels 123, 125 formed in the sleeve 120 to more fully integrate the pressure seals with the sleeve. On the other hand, the pressure seals 140, 141 can be fixed relative to the housing 110, such that the sleeve 120 rotates relative to the pressure seals. In one aspect, the pressure seals 140, 141 can reduce friction between the sleeve 120 and the housing 110 to reduce the force required to rotate the sleeve relative to the housing. Accordingly, the pressure seals 140, 141 can be constructed of PTFE, for example. The pressure seals 140, 141 can be configured as a ring or sheath to extend substantially 360 degrees around the sleeve 120. It should be recognized, however, that the pressure seals 140, 141 can be limited to only a local area about the openings 122, 124 and/or the inlet 112 and the outlet 114. Additional pressure seals 135, 136, 137, 138, 139 can be used, as needed, to provide a sufficient pressure barrier between various components of the sampling device 100. Suitable pressure seals can include O-rings, gaskets, or the like.

The sampling device 100 can further include a coalescent filter 150 disposed in the sleeve 120 between the inlet 112 and the outlet 114. The coalescent filter 150 can be used, for example, to allow a gas to pass through the filter for sampling, while preventing a liquid from passing through. In a conduit carrying primarily gas, for example, the coalescent filter 150 can separate entrained liquid from the gas, such that only gas is sampled from the conduit. The liquid filtered from the gas, or the coalescent material, can then be forcibly removed from the filter by fluid flowing around the filter as the fluid passes from the inlet 112 to the outlet 114. Thus, in other words, the coalescent filter 150 can be configured to allow a sample portion of fluid to pass through the filter for sampling and to allow another portion, or a bypass portion, of fluid to flow past the filter and out of the outlet to carry away coalescent material on the filter. In this way, the coalescent filter 150 is actively cleansed of coalescent material deposited on the filter. The pressure drop between the inlet 112 and the outlet 114 creates an active flow through the housing 110 and around the filter 150 that can remove the coalescent material from the filter. The longitudinal separation between the inlet 112 and the outlet 114, with at least a portion of the filter 150 disposed between, ensures that fluid flow from the inlet to the outlet will sweep across the filter. Thus, coalescent material can be removed from the filter 150 regardless of the direction or effect of gravity on the coalescent material. Accordingly, the sampling device 100 can be oriented in any direction without regard to the direction of gravity and the cleansing action of the fluid flow through the device will still effectively remove coalescent material from the filter 150 and from within the sampling device.

In one aspect, the coalescent filter 150 can be removed from the interior of the housing 110 and/or the sleeve 120. On occasion, it may be useful to remove the coalescent filter 150 from the sampling device 100, such as for inspection or replacement. As illustrated in FIGS. 1A and 1B, the filter 150 can be coupled to the interior support member 160. The interior support member 160 can be coupled to the sleeve 120 via a removable coupling such as a threaded engagement 162. Thus, when in the closed position with the inlet 112 and the outlet 114 sealed, the interior support member 160 can be disengaged from the sleeve 120, and the interior support member with the attached filter 150 can be removed from the sampling device 100. To prepare the sampling device 100 for use, the filter 150 and the interior support member 160 can be inserted into the sleeve 120 and housing 110, and the interior support member 160 can be coupled to the sleeve. Following this, the sleeve 120 can be rotated to the open position to allow fluid to flow into the housing 110 through the inlet 112, whereby fluid can be removed from the interior of the conduit 101 for sampling.

Figure 6:
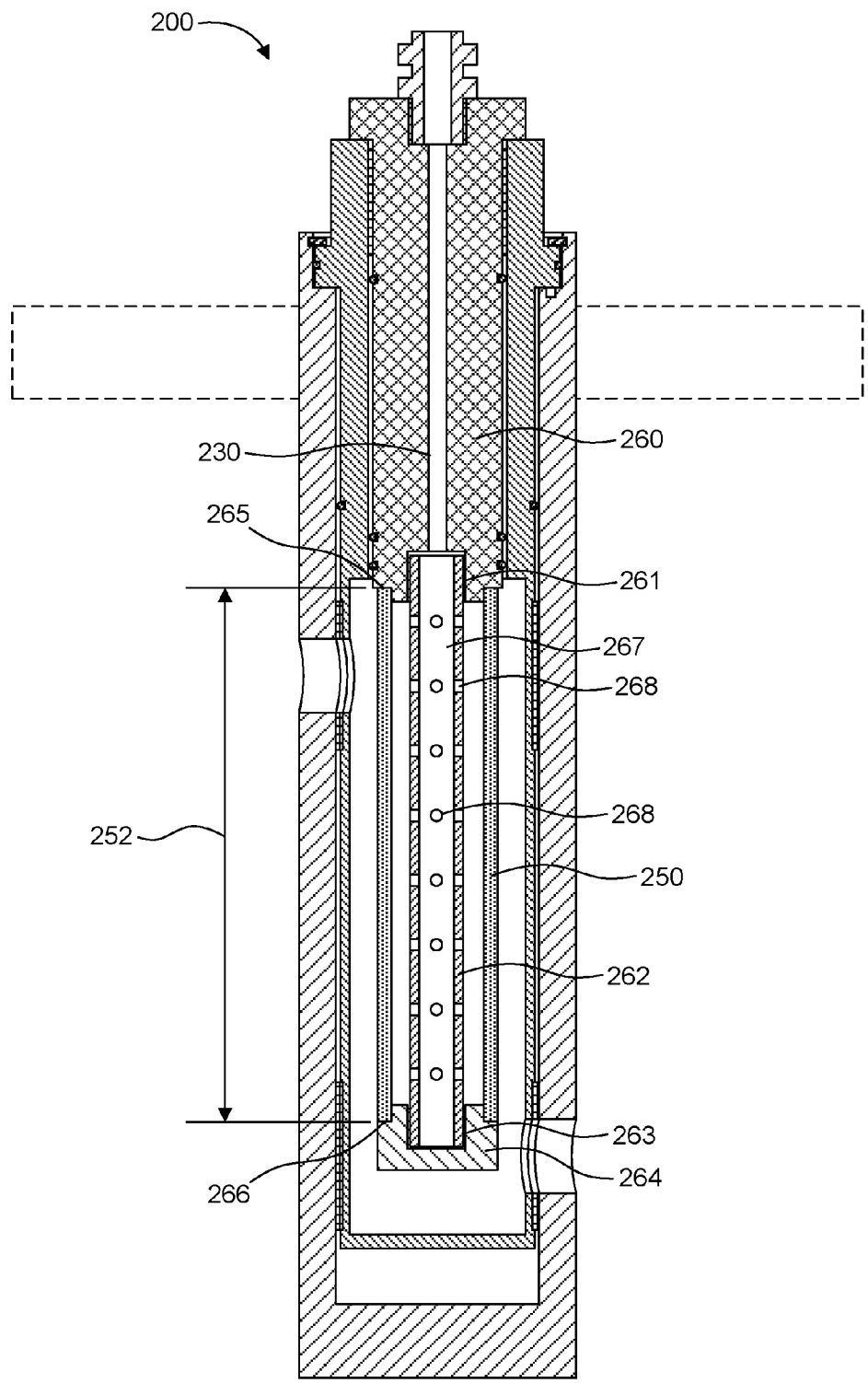
FIG. 6 is a side cross-sectional view of a fluid flow sampling device in accordance with another example of the present disclosure.

Referring to FIG. 6, illustrated is an embodiment of a fluid flow sampling device 200 that demonstrates a coupling between a coalescent filter 250 and an interior support member 260. A filter support member 262 can be disposed inside the filter 250 and coupled to the interior support member 260 at connection 261, which can be a threaded connection. The filter 250 can engage the interior support member 260 with an engagement feature 265. A cap 264 can engage the filter 250 with an engagement feature 266 and can be coupled to the filter support member 262 at connection 263, which can also be a threaded connection. The filter support member 262 can be configured to provide a distance between the engagement points 265, 266 of the interior support member 260 and the cap 264 that is substantially the same as the length 252 of the filter 250. It should be recognized that in some embodiments the interior support member 260 and the filter support member 262 can be integral components. It should also be recognized that in other embodiments the filter support member 262 and the cap 264 can be integral components.

The filter support member 262 can include an interior opening 267 that is in fluid communication with an internal conduit 230. An opening, such as a plurality of holes 268, can fluidly connect an exterior of the filter support member 262 with the interior opening 267. Thus, the filter support member 262 can provide support for the filter 250 and allow fluid to flow through the filter support member for sampling. The holes 268 allow fluid to flow from an exterior of the filter support member to an interior of the filter support member. In operation, fluid that has passed through the filter 250 can enter the interior opening 267 of the filter support member 262 via the holes 268, and then proceed through internal conduit 230 to exit the sampling device 200.

Figure 7A:
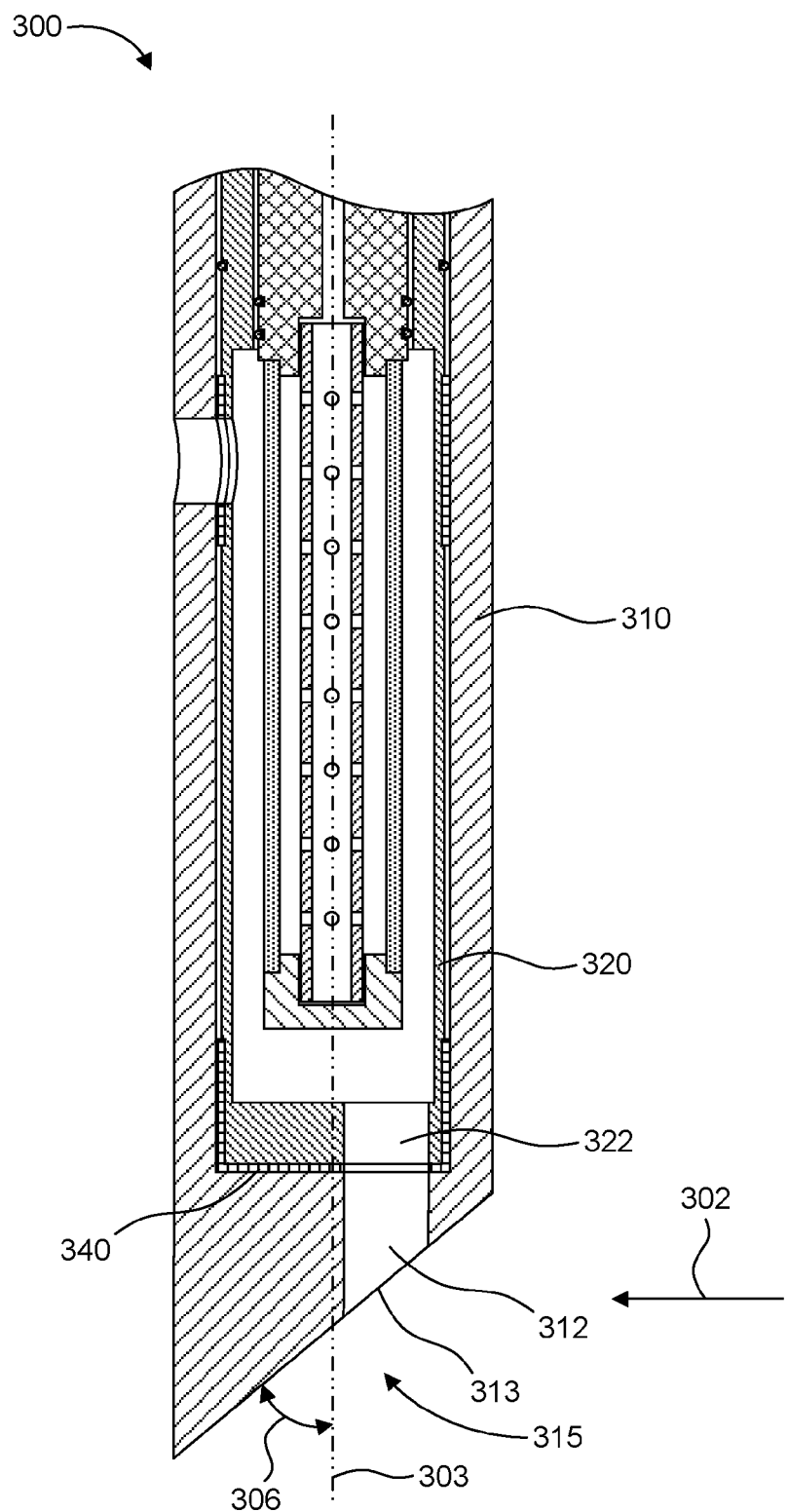
FIG. 7A is a side cross-sectional view of a fluid flow sampling device in an open position in accordance with still another example of the present disclosure.
Figure 7B:
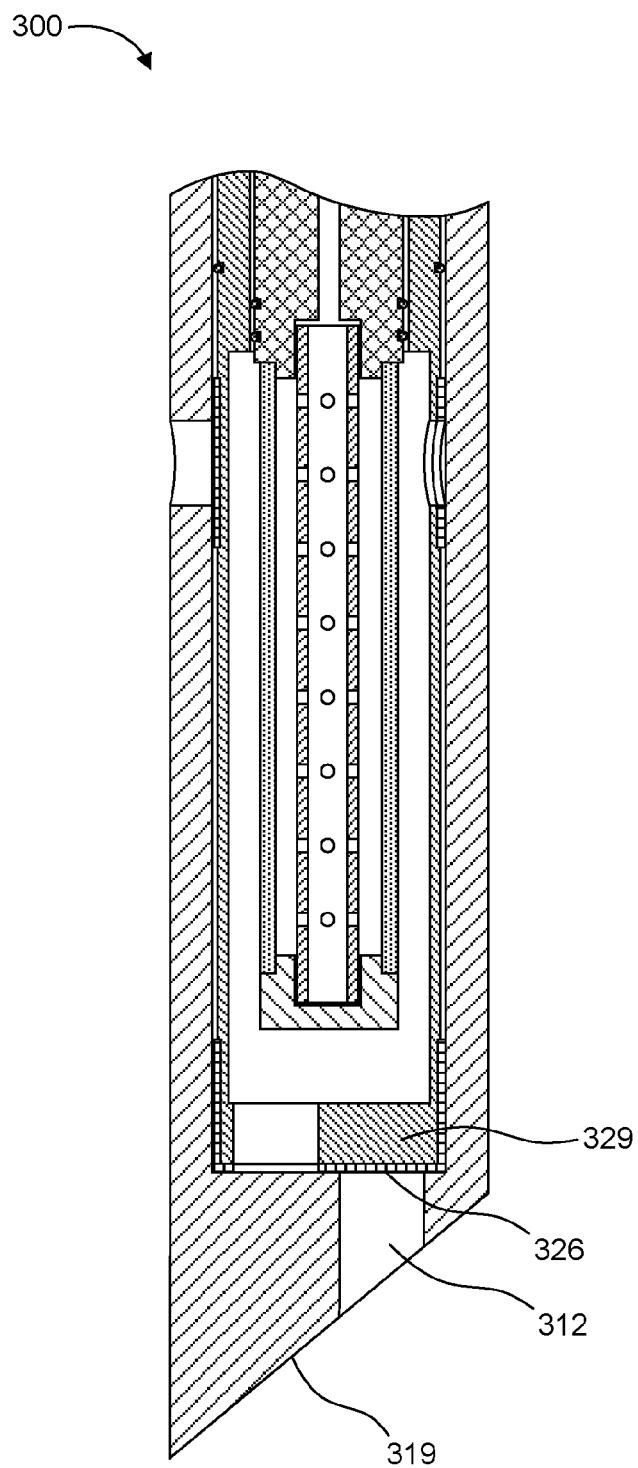
FIG. 7B is the fluid flow sampling device of FIG. 7A in a closed position.
Figures 8A, 8B:
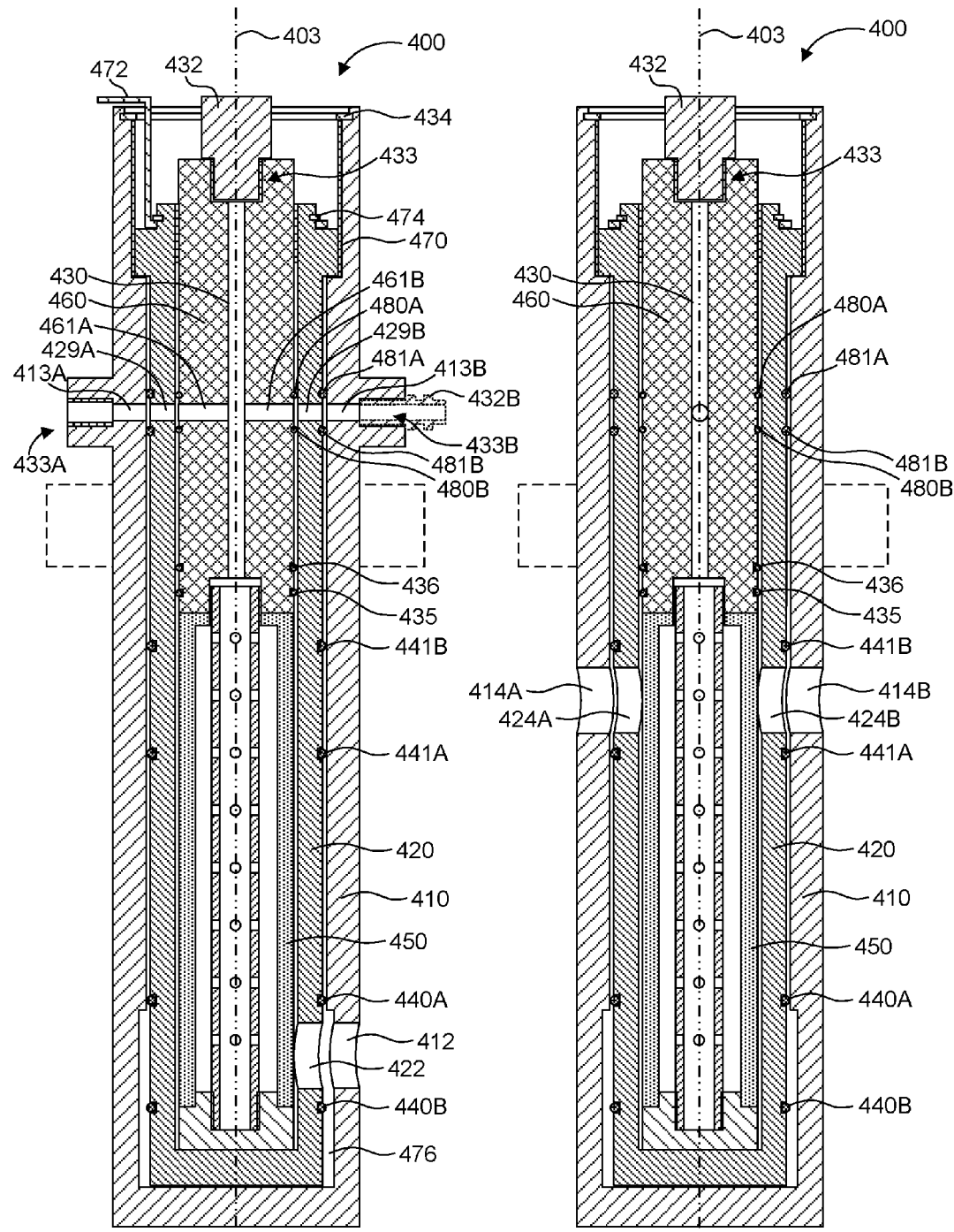
FIG. 8A is a side cross-sectional view of a fluid flow sampling device showing an inlet in an open position in accordance with an additional example of the present disclosure.
FIG. 8B is a side cross-sectional view of the fluid flow sampling device of FIG. 8A showing an outlet in an open position.
Figure 8C:
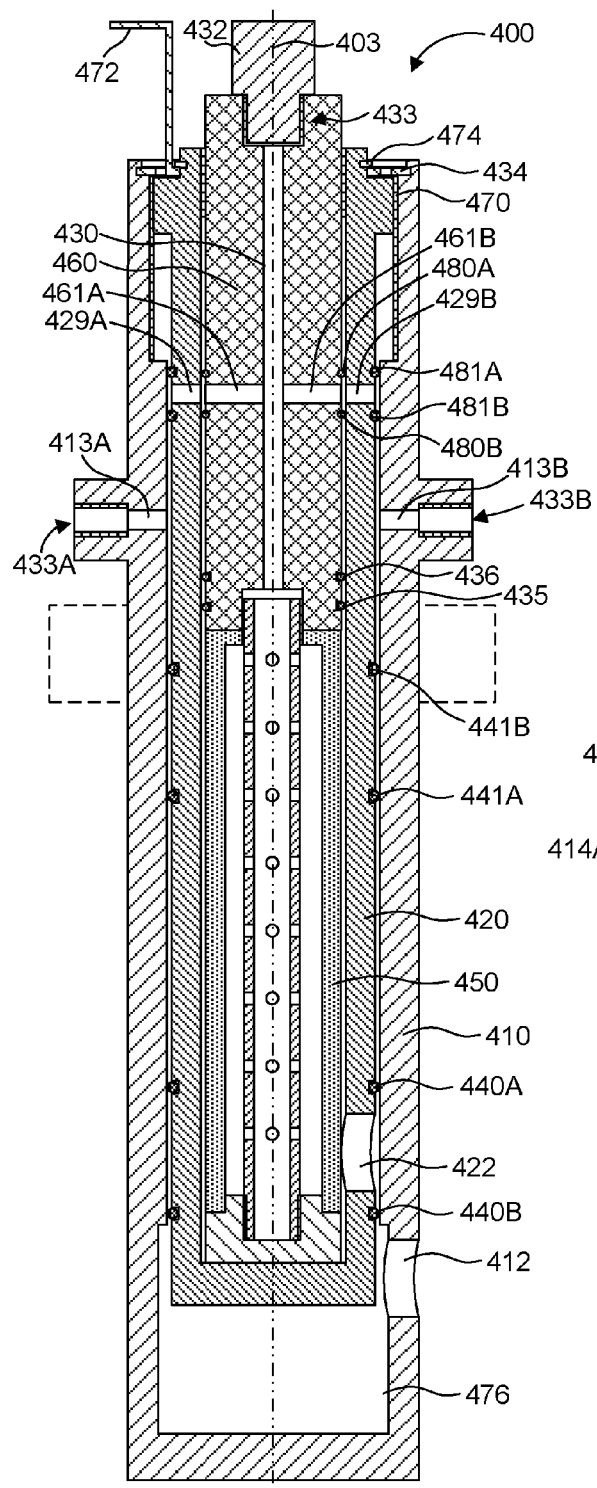
FIG. 8C is a side cross-sectional view of the fluid flow sampling device of FIG. 8A showing the inlet in a closed position.
Figure 8D:
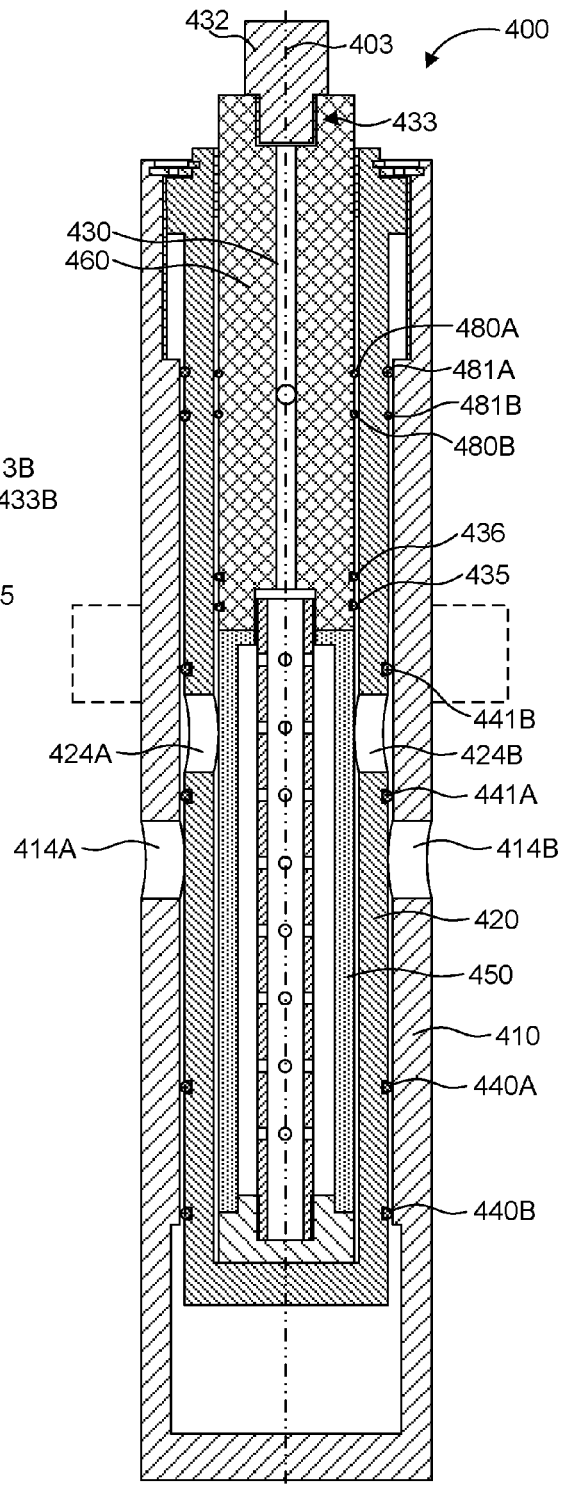
FIG. 8D is a side cross-sectional view of the fluid flow sampling device of FIG. 8A showing the outlet in a closed position.

With reference to FIGS. 7A and 7B, illustrated is a fluid flow sampling device 300 in accordance with an example of the present disclosure. This example illustrates another configuration of an inlet for a sampling device. For simplicity, the conduit and sampling device interface has been omitted. In this example, an inlet 312 is disposed at an end 315 of the housing 310. In one aspect, the inlet can be oriented substantially parallel to longitudinal axis 303.

The sleeve 320 can have an opening 322 corresponding to the inlet 312 of the housing 310. As in the examples discussed above, the sleeve 320 can be rotatable relative to the housing 310 about the axis 303 to an open position (shown in FIG. 7A) and a closed position (shown in FIG. 7B). The open position aligns the opening 322 of the sleeve 320 with the inlet 312 of the housing 310. The closed position blocks the inlet 312 with a portion 326 of the sleeve 320 such that no fluid can flow through the sleeve 320. In order to withstand the fluid pressure acting on the portion 326 of the sleeve, the end 329 of the sleeve can have increased wall thickness. Additionally, pressure seal 340 can be configured to cover the end 329 of the sleeve 320 and optionally a side of the sleeve. Covering the end can contribute primarily to forming a pressure boundary and covering the side can contribute primarily to reducing friction between the sleeve 320 and the housing 310 when the sleeve is rotated.

In one aspect, an end surface 319 of the housing 310 can be at an angle 306 from about 20 degrees to about 70 degrees relative to the axis 303. Such an angle can present an entrance 313 to the inlet 312 that is exposed to fluid flowing in direction 302 toward the inlet.

With reference to FIGS. 8A-8D, illustrated is a fluid flow sampling device 400 in accordance with another example of the present disclosure. The sampling device 400 shares many similarities with the sampling device 200 of FIG. 6. The present example illustrates, among other things, another configuration for a movable sleeve 420 relative to the housing 410. For example, in the sampling device 400, the sleeve 420 can be movable relative to the housing 410 in translation along axis 403 to the open position (showing an inlet of the sampling device in FIG. 8A and an outlet of the sampling device 400 in FIG. 8B) and the closed position (showing an inlet of the sampling device 400 in FIG. 8C and an outlet of the sampling device 400 in FIG. 8D). In one aspect, the sleeve 420 can be movable relative to the housing 410 via a threaded interface 470 between the sleeve and the housing. The threaded interface can facilitate both translational and rotational movement of the sleeve 420 relative to the housing 410. Although a threaded interface is shown and described, it should be recognized that relative translational movement between the sleeve and housing can be accomplished in any suitable manner.

A handle 472 can be included to assist a user in moving the sleeve 420, such as by rotating the sleeve 420 to cause translational movement via the threaded interface 470. It should be recognized that a wrench or the like can be used to rotate the sleeve 420, in which case the sleeve 420 can be configured to interface with a wrench. In the embodiment shown, the handle 472 can be used to cause rotation of the sleeve 420 and resulting translation along the axis 403 via threaded interface 470 with the housing 410. The handle 472 can extend above the housing 410 to allow the user to grasp or interface with the handle. The handle can be integrally formed with the sleeve or a separate component. As shown, the handle 472 is a separate component coupled to the sleeve 420 with a clip 474, such as a C-clip. The interface between the handle 472 and the sleeve 420 can be configured to limit relative rotation between them such that the handle can be used to rotate the sleeve relative to the housing. The housing 410 can also be configured to secure a C-clip 434 that can capture the sleeve 420 within the housing 410. This can prevent unwanted removal or ejection of the sleeve 420 from the housing 410.

As referred to above relative to FIGS. 4A and 4B, the sampling device 400 of FIGS. 8A-8D includes two outlets 414A, 414B. The outlets are shown located 90 degrees about the axis 403 from the inlet 412 and 180 degrees about the axis 403 from one another on opposite sides of the sampling device. This location of the outlets can be at or near a high velocity point in the fluid flowing around the sampling device, which can reduce or minimize buffeting effects from eddy currents.

The sampling device 400 can also include pressure seals 440A, 440B associated with an inlet opening 422 of the sleeve, and pressure seals 441A, 441B associated with outlet openings 424A, 424B of the sleeve. When in the open position, the inlet and outlet opening of the sleeve can be substantially aligned with the inlet 412 and outlets 414A, 414B, respectively. Pressure seals 440A, 441A can be configured to prevent the passage of fluid between interfacing surfaces of the sleeve 420 and the housing 410 that would bypass the inlet and outlet openings 422, 424A, 424B in the sleeve 420. Additionally, pressure seal 441B can be configured to prevent the passage of fluid between the sleeve and the housing that would tend to escape the sampling device via the threaded interface 470.

In operation, the sleeve 420 can be rotated using the handle 472, causing translation of the sleeve along the axis 403 via the threaded interface 470. When the sleeve is moving to the open position, the pressure seals 440A, 440B, 441A, 441B can move or slide past the respective inlet and outlets to form seals between the sleeve and housing, as discussed above. In addition, the sleeve 420 and/or the housing 410 can be configured to form a cavity 476 near the inlet 412 to allow fluid to escape through the inlet as the sleeve is moved along the axis 403 from the closed position to the open position. The cavity can therefore facilitate the escape of fluid, or venting, around the lower pressure seal 440B from the inlet end of the housing that may prevent the sleeve from moving into the open position.

Fluid that enters the housing 410 can be withdrawn from the sampling device 400 by an internal conduit 430. In this case, the internal conduit 130 extends through an interior support member 460 in support of a filter 450 disposed inside a sleeve 420, which can be disposed in the housing 410. The internal conduit 430 can be fluidly coupled to an interior of the housing 410 (or, more specifically in this case, to an interior of the sleeve 420) and to an exterior of the sampling device 400. In one aspect, the sampling device 400 can include one or more sample outlet ports 433, 433A, 433B fluidly coupled to the internal conduit 430 to facilitate removal of fluid from the sampling device and that can interface with a tube or pipe (not shown) for transporting a fluid sample from the device 400 to a reservoir or testing station for analysis. For example, the "top" sample outlet port 433, which is substantially aligned with the longitudinal axis 403, can be integrally formed with the interior support member 460. In one aspect, the top sample outlet port 433 can be formed in, or associated with, a top of the interior support member 460. In addition, the "side" sample outlet ports 433A, 433B, which are off-axis or substantially perpendicular to the longitudinal axis 403, can be fluidly coupled to the internal conduit 430 when in the open position via a lateral conduit 413A, 413B in the housing 410 aligned with a lateral conduit 429A, 429B in the sleeve 420 in fluid communication with a lateral conduit 461A, 461B in the interior support member 460. The lateral conduits can be substantially perpendicular to the internal conduit 430. In one aspect, the side sample outlet ports 433A, 433B can be formed in, or associated with, a side of the housing 410. In one example, the side sample outlet ports can include, similar to that shown in FIG. 1 at reference numeral 132, a fitting 432B (shown in phantom lines FIG. 8A at one location, but which could be at any outlet port location) coupled to the sample outlet port configured to allow for removal of the sampling portion of the fluid from the sampling device for sampling.

Pressure seals 480A, 480B can be disposed between the interior support member 460 and the sleeve 420, and pressure seals 481A, 481B can be disposed between the sleeve 420 and the housing 410. The pressure seals 480A, 480B, 481A, 481B can provide a pressure barrier between the respective components to facilitate passage of a fluid sample from the internal conduit 430 to the sample outlet ports 433A, 433B without leakage. Additional pressure seals 435, 436 can be used, as needed, to provide a sufficient pressure barrier between various components of the sampling device 400. Suitable pressure seals can include O-rings, gaskets, or the like. A cap or plug 432 can be used to close one or more of the sample outlet ports when not in use, as illustrated with the cap 432 attached to the top sample outlet port 433.

When in the closed position, unlike the open position, the sleeve 420 is positioned such that the inlet opening 422 and the outlet openings 424A, 424B are not aligned with the inlet 412 and outlets 414A, 414B, respectively. Pressure seal 440B can be configured to minimize or prevent the passage of fluid between the sleeve 420 and the housing 410 that would tend to pass through the inlet opening 422 of the sleeve. Similarly, pressure seal 441A can be configured to minimize or prevent the passage of fluid between the sleeve 420 and the housing 410 that would tend to pass through the outlet opening 414A, 414B of the sleeve. Thus, the sleeve can block or prevent the flow of fluid through the inlet 412 and outlets 414A, 414B of the sampling device. In addition, the pressure seals 441A, 441B associated with the outlet openings 424A, 424B of the sleeve and the pressure seals 481A, 481 B associated with the side sample outlet ports 433A, 433B can be configured to prevent the passage of fluid between the sleeve 420 and the housing 410 that would tend to escape from the sampling device 400 as well as isolate the side sample outlet ports 433A, 433B from internal pressure and fluids. The pressure seals can also minimize or prevent leakage of fluid between the sleeve 420 and the housing 410 tending to enter or exit the sleeve via the sleeve openings (i.e., the inlet 412 or the outlet 414A, 414B), as well as the lateral conduit 429A, 429B of the sampling device 400. As shown, the pressure seals are configured as O-rings disposed between the sleeve 420 and the housing 410, although any suitable seal can be used.

This pressure seal configuration can also provide some redundancy to account for a faulty seal. For example, if pressure seal 440B leaks, then fluid can enter the inlet opening 422, but is blocked from the side sample outlet ports 433A, 433B by the pressure seals 481B, while the pressure seal 481A prevents fluid from escaping the sampling device 400. In addition, if one or both of the pressure seals 440A, 441A leaks, then the pressure seal 441B can prevent fluid from reaching the side sample outlet ports 433A, 433B. Conversely, if the pressure seal 441B is faulty, fluid can be prevented from reaching the side sample outlet ports 433A, 433B by one or both of the pressure seals 440A, 441A.

In one aspect, the sampling device 400 can be configured to facilitate safe removal of the filter 450, such as for maintenance. For example, a pressure gage can be coupled to any one of the top or side sample outlet ports 433, 433A, 433B and a valve, such as a vent or bleed valve, can be coupled to another of the sample outlet ports to facilitate "bleeding" pressure from the sampling device 400 when in the closed position. In one example, the pressure gage can be coupled to a side sample outlet port 433A, 433B and the valve can be coupled to the top sample outlet port 433. In another example, the pressure gage can be coupled to a top sample outlet port 433 and the valve can be coupled to the side sample outlet port 433A, 433B. An increase in pressure over time would indicate that one of the pressure seals is faulty and appropriate action should be taken prior to removing the filter. If there is no pressure buildup, then the pressure seals are intact and the filter may be safely removed. In one aspect, the other sample outlet port can be used to purge the attached sample system, or coupled to a gas detection system to check for the release of toxic gas.

Figure 9:
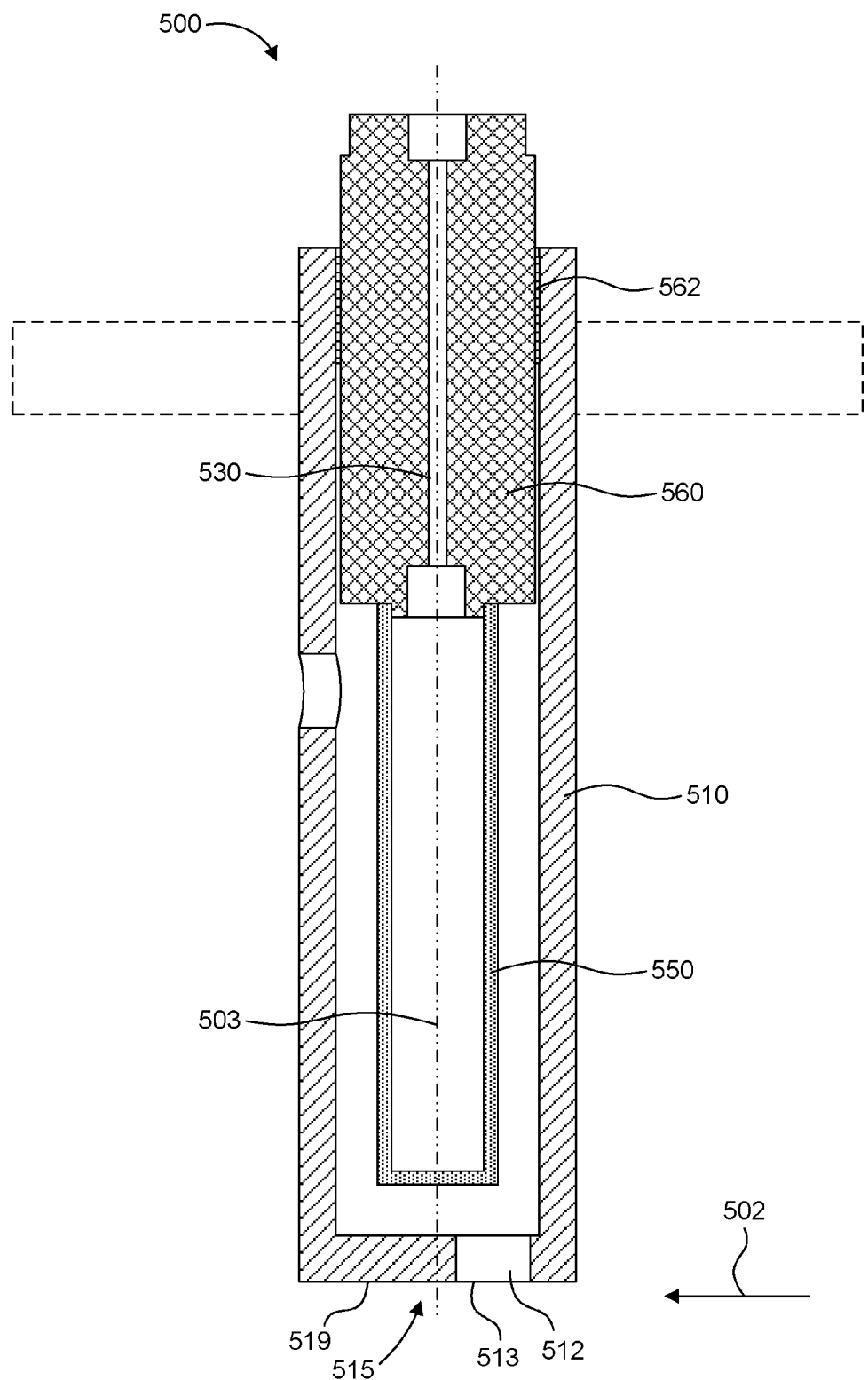
FIG. 9 is a side cross-sectional view of a fluid flow sampling device in accordance with yet another example of the present disclosure.

With reference to FIG. 9, illustrated is a fluid flow sampling device 500 in accordance with an example of the present disclosure. This example illustrates a sampling device that does not include a sleeve. The simplified sampling device 500 includes a housing 510, and a filter 550 that are similar in many respects to those described above. The filter 550 is coupled to an interior support member 560, which includes an internal conduit 530. In this example, however, the interior support member 560 is coupled directly to the housing 510, in the absence of a sleeve. The coupling between the interior support member 560 and the housing 510 can be a threaded connection 562 or any other suitable connection. Thus, the internal support member 560 and the filter 550 can be removed from inside the housing 510.

The sampling device 500 also illustrates another embodiment of an inlet for the sampling device. As in the example illustrated in FIGS. 7A and 7B, inlet 512 is disposed at an end 515 of the housing 510. However, in this example, an end surface 519 of the housing 510 is substantially perpendicular to the axis 503. Thus, little, if any, of the entrance 513 to the inlet 512 is exposed to fluid flowing in direction 502 toward the inlet.

Figure 10:
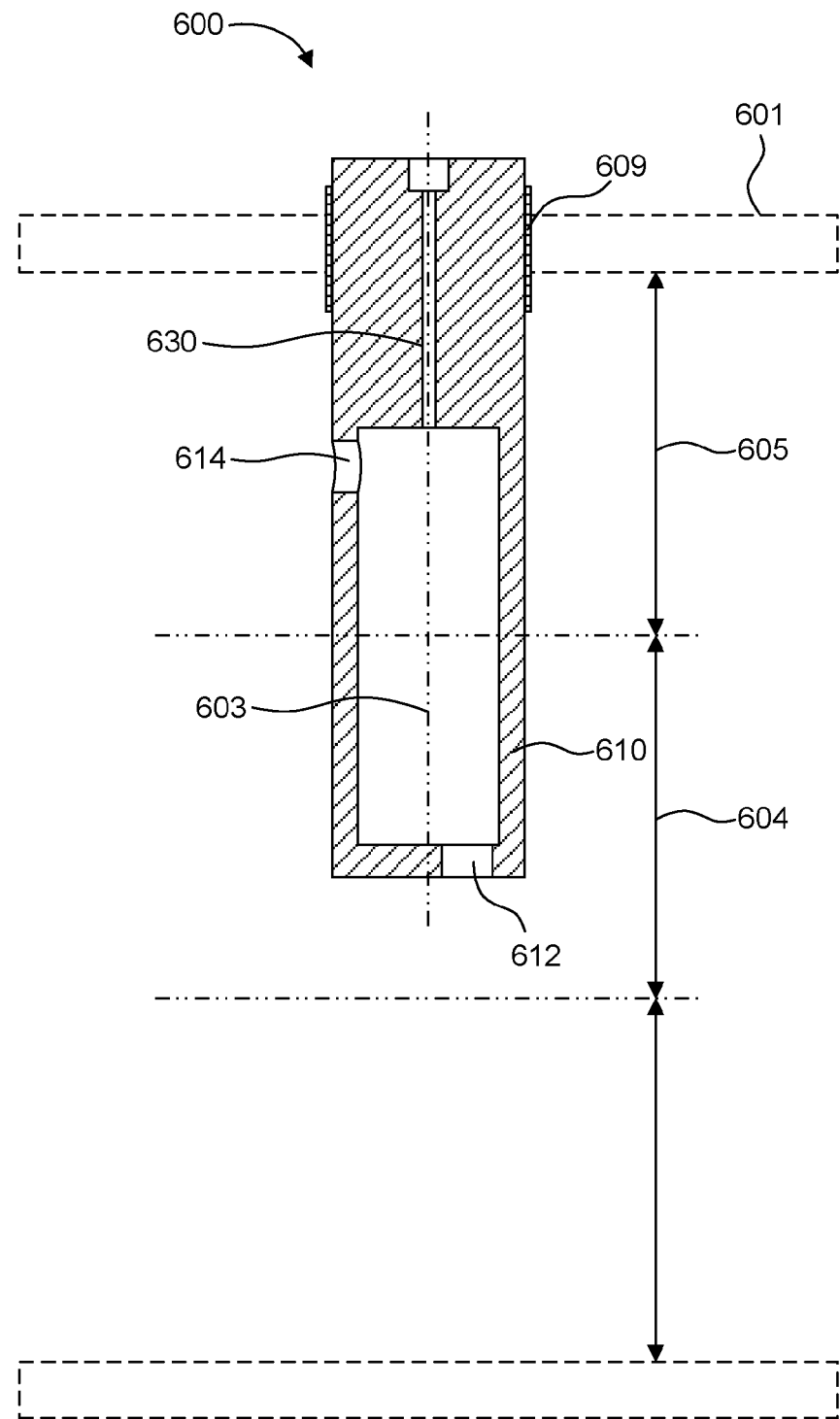
FIG. 10 is a side cross-sectional view of a fluid flow sampling device in accordance with still another example of the present disclosure.

With reference to FIG. 10, illustrated is a fluid flow sampling device 600 in accordance with an example of the present disclosure. This example illustrates a sampling device that does not include a sleeve or a filter. The simplified sampling device 600 includes a housing 610 and an internal conduit 630. As in other examples disclosed herein, the housing 610 includes a fluid inlet 612 and a fluid outlet 614 longitudinally separated from one another along an axis 603 of the housing. A coupling portion 609 on the housing 610 can couple the fluid flow sampling device 600 to a fluid conduit 601 and position the fluid inlet 612 in a middle third 604 of the fluid conduit 601. Additionally, the fluid outlet 614 can be positioned in an upper third 605 of the fluid conduit 601. The fluid inlet 612 and the fluid outlet 614 can be fluidly coupled to one another such that a portion of fluid flow in the fluid conduit enters the inlet, flows through the housing, and exits the outlet. Another portion of the fluid flow is extractable from within the housing 610 to a location outside of the fluid conduit 601.

Figure 11:
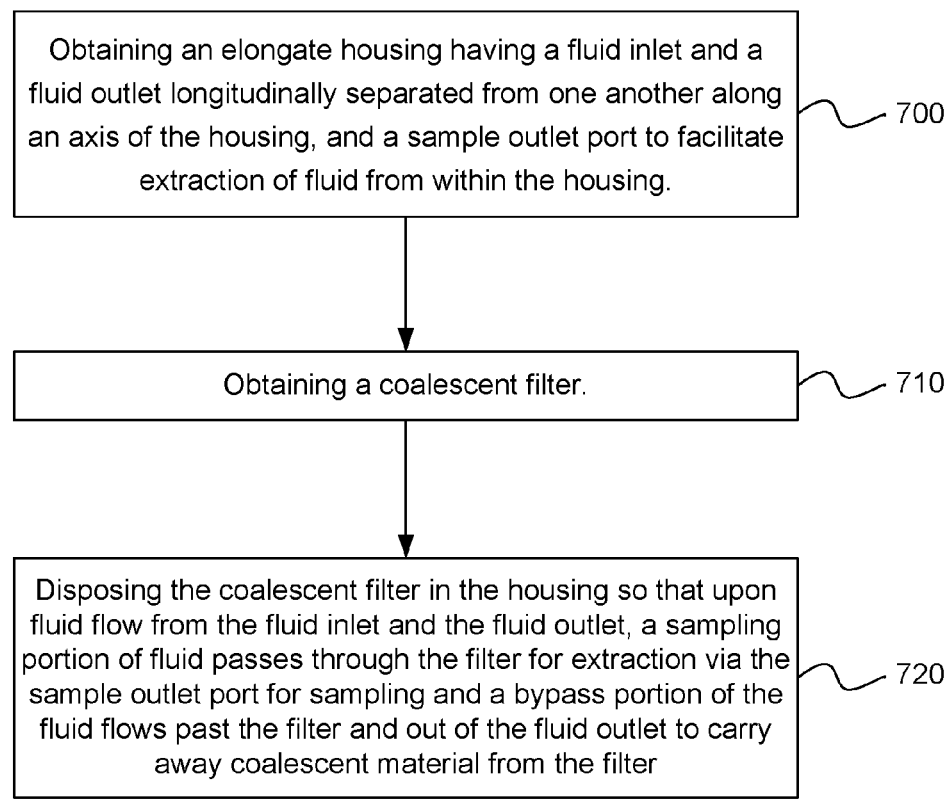
FIG. 11 is a flow diagram of a method in accordance with an example of the present disclosure.

In a related embodiment, and to reiterate to some degree, a method for configuring a fluid flow sampling device in accordance with the principles herein is shown in FIG. 11. The method comprises obtaining a housing having a fluid inlet and a fluid outlet longitudinally separated from one another along an axis of the housing, and a sample outlet port to facilitate extraction of fluid from within the housing 700. The method further comprises obtaining a coalescent filter 710. Additionally, the method comprises disposing the coalescent filter in the housing so that upon fluid flow from the fluid inlet and the fluid outlet, a sampling portion of fluid passes through the filter for extraction via the sample outlet port for sampling and a bypass portion of the fluid flows past the filter and out of the fluid outlet to carry away coalescent material from the filter 720. It is noted that no specific order is required in this method, though generally in one embodiment, these method steps can be carried out sequentially.

In one aspect, the method further comprises obtaining a sleeve having openings corresponding to the inlet and the outlet of the housing, the sleeve being rotatable relative to the housing about the axis to an open position and a closed position, wherein the open position aligns the openings of the sleeve with the inlet and the outlet of the housing to allow fluid to flow into the inlet, through the sleeve, and out of the outlet, and wherein the closed position blocks the inlet and the outlet with a portion of the sleeve such that no fluid can flow through the sleeve. In another aspect, the method further comprises disposing the sleeve in the housing. In an additional aspect, the method comprises disposing the coalescent filter in the sleeve.

While the foregoing examples are illustrative of the principles and concepts discussed herein, it will be apparent to those of ordinary skill in the art that numerous modifications in form, usage and details of implementation can be made without the exercise of inventive faculty, and without departing from those principles and concepts. Accordingly, it is not intended that the principles and concepts be limited, except as by the claims set forth below.

What is claimed is:

1. A fluid flow sampling device for positioning in a fluid conduit, comprising:
   a housing having a fluid inlet and a fluid outlet longitudinally separated from one another along an axis of the housing, the fluid inlet positionable in a middle third of the fluid conduit;
   a coalescent filter disposed between the fluid inlet and the fluid outlet to allow a sampling portion of fluid to pass through the filter and to allow a bypass portion of the fluid to flow past the filter and out of the fluid outlet to carry away coalescent material from the filter;
   a sample outlet port comprising a fitting coupled to the sample outlet port configured to allow for removal of the sampling portion of the fluid from the sampling device for sampling; and
   a sleeve disposed in the housing that is movable to block or allow flow through the fluid inlet and the fluid outlet, the sleeve comprising a lateral conduit corresponding to the sample outlet port, wherein when flow is allowed through the fluid inlet, the lateral conduit is aligned with the sample outlet port to facilitate removal of the sampling portion of the fluid from the sampling device.

2. The fluid flow sampling device of claim 1, wherein the sample outlet port is on a side of the housing.

3. The fluid flow sampling device of claim 1, further comprising at least one seal disposed between the sleeve and the housing to minimize fluid leakage between the sleeve and the housing tending to escape from the sampling device.

4. The fluid flow sampling device of claim 1, wherein the housing comprises an elongate configuration to facilitate longitudinal separation of the fluid inlet and the fluid outlet.

5. A method for configuring a fluid flow sampling device, comprising:
   obtaining a housing having:
      a fluid inlet and a fluid outlet longitudinally separated from one another along an axis of the housing, and
      a sample outlet port comprising a fitting coupled to the sample outlet port to facilitate extraction of fluid from within the housing;
   obtaining a coalescent filter;
   disposing the coalescent filter in the housing so that upon fluid flow from the fluid inlet and the fluid outlet, a sampling portion of fluid passes through the filter for extraction via the sample outlet port for sampling and a bypass portion of the fluid flows past the filter and out of the fluid outlet to carry away coalescent material from the filter;
   obtaining a sleeve having openings corresponding to the fluid inlet and the fluid outlet of the housing, the sleeve being movable relative to the housing to an open position and a closed position, wherein the open position aligns the openings of the sleeve with the fluid inlet and the fluid outlet of the housing to allow fluid to flow into the fluid inlet, through the sleeve, and out of the fluid outlet, and wherein the closed position blocks the fluid inlet and the fluid outlet with a portion of the sleeve such that fluid is prevented from flowing through the sleeve, the sleeve having a lateral conduit corresponding to the sample outlet port, wherein when flow is allowed through the fluid inlet, the lateral conduit is aligned with the sample outlet port to facilitate removal of the sampling portion of the fluid from within the housing; and
   disposing the sleeve in the housing at least substantially around the coalescent filter.

6. The method of claim 5, further comprising at least one seal disposed between the sleeve and the housing to minimize fluid leakage between the sleeve and the housing tending to escape from the sampling device.

7. A fluid flow sampling device for positioning in a fluid conduit, comprising:
   a housing having a fluid inlet and a fluid outlet longitudinally separated from one another along an axis of the housing, the fluid inlet positionable in a middle third of the fluid conduit;
   a coalescent filter disposed between the fluid inlet and the fluid outlet to allow a sampling portion of fluid to pass through the filter and to allow a bypass portion of the fluid to flow past the filter and out of the fluid outlet to carry away coalescent material from the filter;
   a sample outlet port on a side of the housing to facilitate removal of the sampling portion of the fluid from the sampling device for sampling; and
   a sleeve disposed in the housing that is movable to block or allow flow through the fluid inlet and the fluid outlet, the sleeve comprising a lateral conduit corresponding to a sample outlet port, wherein when flow is allowed through the fluid inlet, the lateral conduit is aligned with the sample outlet port to facilitate removal of the sampling portion of the fluid from the sampling device.

8. The fluid flow sampling device of claim 7, further comprising at least one seal disposed between the sleeve and the housing to minimize fluid leakage between the sleeve and the housing tending to escape from the sampling device.

9. A method for configuring a fluid flow sampling device, comprising:
   obtaining a housing having:
      a fluid inlet and a fluid outlet longitudinally separated from one another along an axis of the housing, and
      a sample outlet port to facilitate extraction of fluid from within the housing;
   obtaining a coalescent filter;
   disposing the coalescent filter in the housing so that upon fluid flow from the fluid inlet and the fluid outlet, a sampling portion of fluid passes through the filter for extraction via the sample outlet port for sampling and a bypass portion of the fluid flows past the filter and out of the fluid outlet to carry away coalescent material from the filter;
   obtaining a sleeve having openings corresponding to the fluid inlet and the fluid outlet of the housing, the sleeve being movable relative to the housing to an open position and a closed position, wherein the open position aligns the openings of the sleeve with the fluid inlet and the fluid outlet of the housing to allow fluid to flow into the fluid inlet, through the sleeve, and out of the fluid outlet, and wherein the closed position blocks the fluid inlet and the fluid outlet with a portion of the sleeve such that fluid is prevented from flowing through the sleeve, the sleeve having a lateral conduit corresponding to the sample outlet port, wherein when flow is allowed through the fluid inlet, the lateral conduit is aligned with the sample outlet port to facilitate removal of the sampling portion of the fluid from within the housing; and
   disposing the sleeve in the housing at least substantially around the coalescent filter.

10. The method of claim 9, further comprising at least one seal disposed between the sleeve and the housing to minimize fluid leakage between the sleeve and the housing tending to escape from the sampling device.

* * * * *